US00PP09623P

United States Patent [19]

Gruppe et al.

[11] Patent Number: Plant 9,623

[45] Date of Patent: Aug. 13, 1996

[54] CHERRY ROOTSTOCK GI 148/9

[75] Inventors: Werner Gruppe, Linden/Grossen/Linden; Hanna Schmidt, Ahrensburg, both of Germany

[73] Assignee: Inter-Plant Patent Marketing, Inc., Ontario, Canada

[21] Appl. No.: 485,403

[22] Filed: Jun. 7, 1995

[51] Int. Cl.[6] ..... A01H 5/00

[52] U.S. Cl. ..... Plt./37

[58] Field of Search ..... Plt./37

[56] References Cited

U.S. PATENT DOCUMENTS

P.P. 8,852 8/1994 Gruppe et al. ..... Plt./37

P.P. 8,954 10/1994 Gruppe et al. ..... Plt./37

OTHER PUBLICATIONS

Perry, R. L., "Cherry Rootstocks", Rootstocks for Fruit Crops, 1987, John Wiley & Sons, pp. 251–254.

*Primary Examiner*—James R. Feyrer
*Attorney, Agent, or Firm*—Flynn, Thiel, Boutell & Tanis P.C.

[57] ABSTRACT

The new and distinct cultivar of cherry rootstock, which has been given the designation GI 148/9 produces a tree which is generally spreading and which upon grafting produces a dwarf tree.

2 Drawing Sheets

FIELD OF THE INVENTION

The present invention relates generally to cherry trees and more specifically to a new and distinct variety of cherry hybrid tree which is particularly useful as a rootstock.

BACKGROUND OF THE INVENTION

The use of cherry hybrid trees as rootstock is known in the art of producing cherry trees. One such variety is F12/1, a vegetatively propagated P. avium-selection. Cherry rootstock varieties GI 148/1 and 148/8 are described in U.S. Plant Pat. Nos. 8,852 and 8,954. The use of cherry hybrid varieties as rootstock produces a dwarf tree that comes into earlier and heavier bearing without sacrificing fruit size.

SUMMARY OF THE INVENTION

The new and distinct cultivar of cherry rootstock, which has been given the designation GI 148/9 produces a tree which is generally spreading and which upon grafting produces a dwarf tree.

Figure 1:
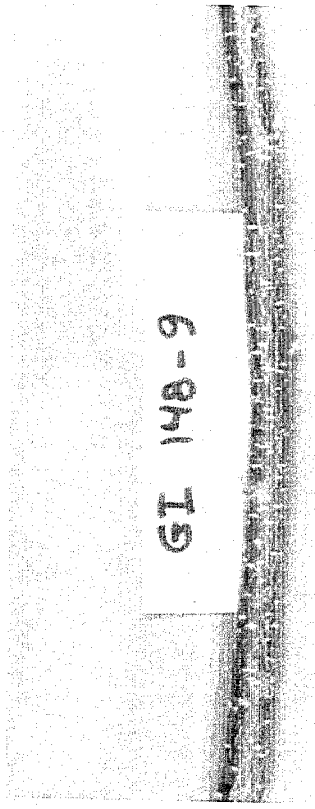
FIG. 1 illustrates a branch and dormant lateral buds, bark and lenticels of GI 148/9.
Figure 2:
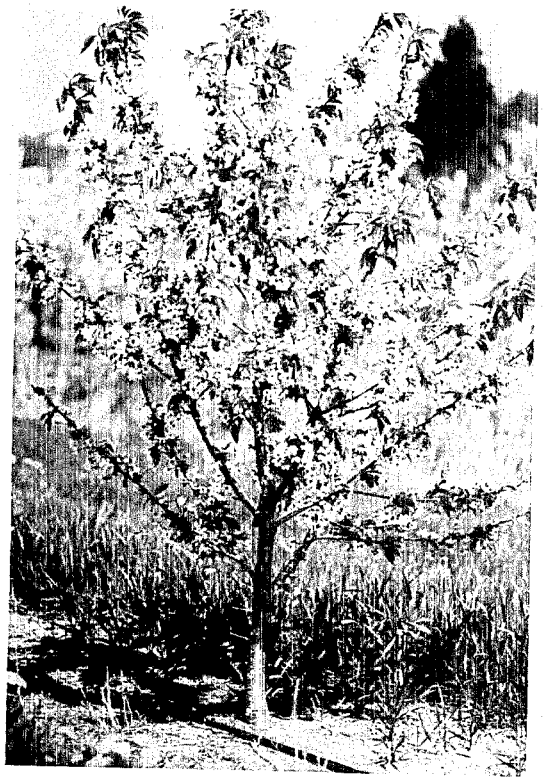
FIG. 2 is a whole tree view of 148/9.

The new and distinct variety of cherry hybrid tree of the present invention was bred by the inventors as a cross of *Prunus cerasus* cv. "Schattenmorelle" with *Prunus canescens* in Giessen, Germany. It has been successfully asexually propagated by softwood cuttings at the University of Giessen in Giessen, Germany, and has been observed to remain true to the description set forth herein.

DETAILED DESCRIPITION OF THE INVENTION

GI 148/9 as used as a rootstock for sweet cherry trees induces dwarfing to a significant degree. In comparison with rootstock F12/1, GI 148/9 produces 29 percent of growth, as measured as the fresh weight of the upper tree parts of cv. "Hedelfinger" after 12 years in orchards near Giessen, Germany. Precocity, high production of fruit and yield efficiency, good fruit size and no or very few suckers were induced. GI 148/9 as a rootstock confers earlier and heavier bearing to the scion as compared to F12/1 clonal cherry rootstock. In one trial, it induced a yield in the variety "Hedelfinger" in the 5th leaf of 5.8 kg/tree (cf. F12/1:0.2 kg/tree) and in the 7th leaf of 13.8 kg/tree (cf. F12/1:5.7 kg/tree). As a mean of seven years, 100-fruit-weight of "Hedelfinger" grafted on 148/9 was 763 grams, while 100-fruit-weight of "Hedelfinger" grafted on F12/1 was 735 grams.

GI 148/9 itself is of medium vigor, has a spreading habit and long, thin partly drooping branches. After eight growing seasons near Giessen, Germany, GI 148/9 demonstrated a height of 3.40 meters and a width of 3.85 meters. It is tolerant to the virus PDV, sensitive to the virus PNRV and medium tolerant to Pfeffinger Disease Its tolerance towards water-logging and its frost-hardiness is medium.

The following varieties of sweet and sour cherries have been successfully grafted onto GI 148/9: Abels Spaete, Büttners Rote Knorpel, Grosse Schwarze Knorpel, Van, Gold, Hedelfinger, Hedelfinger Hilltop, Ulster, Valeska, Bing, Early Burlat, Emperor Francis, Königskirsche, Meckenheimer, Oktavia, Regina, Schneiders Späte Knorpel, Stella, Windsor, Montmorency. No graft incompatibility is presently known.

Ploidy of 148/9 is probably triploid (2n=3×). The ploidy status of the parents has been investigated by isoenzyme analysis and is tetraploid (2n=4×) for the mother plant= *Prunus cerasus*, "Schattenmorelle", and diploid (2n=2×) for the father plant, *Prunus canescens*.

Leaves:

*Overall shape.*—Obvate.

*Apex shape.*—Acute to slightly acuminate.

*Base shape.*—Rounded, slightly acuminate.

*Leaf serration.*—Doubly serrate leaf margin.

*Veination.*—Pinnate, 10–12 major veins, mainly alternate.

*Stipules.*—Prominent, pointed, attached to base of petiole.

*Glands.*—Rounded, usually 3, sometimes 2 or 4 attached to bottom edge blade or petiole close to blade.

*Pubescence.*—Very slightly pubescent on adaxil surface (top), fairly obvious pubescent on abaxil surface especially along veins.

*Color.*—Light green.

Leaf dimensions at 5th and 9th:

| | 5th leaf | 9th leaf |
|---|---|---|
| Mean length of leaves | 83 mm | 80 mm |
| Mean width of leaves | 42 mm | 50 mm |
| Mean length of petioles | 12 mm | 10 mm |

Branches:

*Thickness of one year branch.*—22 mm diameters.

*Color of 2-year old branch.*—greyed orange, Fan 4, 173-A (R.H.S. color chart)

*Overall.*—1-Year old branches are very slightly pubescent, buds alternate on branch; 1-year old branches with cream colored lenticels 0.5 mm diameter.

Branch dimensions (For a single GI 148/9 plant in the ungrafted condition after the 5th leaf; in brackets, comparable data for F12/1):

*Mean length of 1-year-old branches.*—21.6 cm (19.8 cm).

*Mean length of 2-year-old branches.*—24.8 cm (35.0 cm).

*Mean length of 3-year-old branches.*—54.4 cm (63.2 cm).

*Mean diameter of 1-year-old branches.*—2.2 cm (3.4 mm).

*Mean diameter of 2-year-old branches.*—3.4 mm (5.8 mm).

*Mean diameter of 3-year-old branches.*—6.2 mm (10.1 mm).

*Mean no. of branches from 2-year-old branches.*—0 (0.7).

*Mean no. of branches from 3-year-old branches.*—2.6 (2.4).

*Mean no. of nodes of 2-year-old branches.*—17.4 (15.3).

*Mean no. of nodes of 3-year-old branches.*—20.2(22.4).

*Mean angle of 3-year-old branches.*—61.3 (59.7).

*Mean angle of 4-year-old branches.*—55.0 (58.3).

Buds: Conical, acute, adpressed, 3–4 mm long, prominent leaf scars.

Flowers:

*Flowering.*—Flowering started in the first year.

*Abundance.*—Flowering became abundant during third year.

*Petal color.*—White.

*Petal shape.*—Oblong.

*Petal length/width ratio.*—Approximately 1.5:1.

Bloom: Time of bloom is very late.

Overall vigor:

*Ungrafted.*—Medium.

*Suckers.*—None or very few.

Root system: A comparison of the root systems of GI 148/9 grafted "Hedelfinger" and F12/1 grafted with "Hedelfinger" is shown below in Table 1:

TABLE 1

| | GI 148/9 | F12/1 |
|---|---|---|
| Fresh Matter (kg)/13.8 m3 soil | 26.6 | 103.9 |

TABLE 1-continued

| | GI 148/9 | F12/1 |
|---|---|---|
| Dry Matter (kg)/13.8 m3 soil | 14.7 | 51.3 |
| Total length of roots (m)/13.8 m3 soil | 1615 | 1379 |
| Dry Matter/root length (g) | 9.1 | 37.6 |

GI 148/9 has a more dense root system than F12/1 and a much higher portion of fine roots.

Survey of growth data: Growth of one ungrafted clone, 60 kilometers south of Giessen, Germany at about 5th and 9th leaf is shown in Table 2 below:

TABLE 2

| | 5th leaf | 9th leaf |
|---|---|---|
| Height | 210 | 340 |
| Width (cm) | 230 | 400 |
| Depth (cm) | | 370 |
| Fresh Weight (kg) | | 19.0 |

In Table 3 the growth results after 12 years of GI 148/9 and F12/1, both grafted with Hedelfinger.

TABLE 3

| | GI 148/9 | F12/1 |
|---|---|---|
| Height of Crown (m) | 3.0 | 5.2 |
| Width of Crown (m) | 4.7 | 6.2 |
| Stem Cross Sectional (cm2) Area of Variety | 245.9 | 503.4 |
| Stem Cross Sectional (cm2) Area of Rootstock | 778.8 | 486.0 |
| Fresh Weight of Plant Parts Above Ground | 54.5 | 726.3 |
| Weight in Percent | 37.0 | 100.0 |

A Crown-silhouette comparison of GI 148/9 and F12/1 (m2)=height×(with+depth)/2: is shown in Table 4.

TABLE 4

| | GI 148/9 | F12/1 |
|---|---|---|
| After 4 years in orchard: | 3.5 | 7.7 |
| After 6 years in orchard: | 6.1 | 14.3 |

Enzyme polymorphism of GI 148/2: (Studied by horizontal starch gel electrophoresis of leaf tissue of 8 loci.) are shown in Table 5.

TABLE 5

| | 148/9 |
|---|---|
| Aconitase-2 | 2 |
| Alkoholdehydrogenase-1 | 7 |
| Isocitratdehydrogenase-2 | 772 |
| Leucinaminopeptisase-1 | 34 |
| 5-Phosphogluconat-Dehydrogenase-1 | 772 |
| 6-Phosphogluconat-Dehydrogenase-2 | 722 |
| Phophoglucose-Isomerase-2 | 224 |
| Phosphoglucomutase-2 | 25 |

What is claimed is:

1. A new and distinct variety of cherry hybrid tree as shown and described herein.

* * * * *